(12) United States Patent
Sawano et al.

(10) Patent No.: US 6,552,211 B2
(45) Date of Patent: Apr. 22, 2003

(54) ZIRCONIUM COMPOUND AND ELECTROPHOTOGRAPHIC TONER EMPLOYING IT

(75) Inventors: Masataka Sawano, Tsukuba (JP); Taito Muraoka, Tsukuba (JP); Katuya Yamaguti, Tsukuba (JP); Rie Murakami, Tsukuba (JP); Hiroyoshi Yamaga, Tsukuba (JP)

(73) Assignee: Hodogaya Chemical Co., Ltd., Kawasaki (JP)

( * ) Notice: Subject to any disclaimer, the term of this patent is extended or adjusted under 35 U.S.C. 154(b) by 149 days.

(21) Appl. No.: 09/739,773

(22) Filed: Dec. 20, 2000

(65) Prior Publication Data

US 2001/0010887 A1 Aug. 2, 2001

Related U.S. Application Data (62) Division of application No. 09/297,568, filed as application No. PCT/JP98/03953 on Sep. 3, 1998, now Pat. No. 6,410,198.

(30) Foreign Application Priority Data

Sep. 5, 1997 (JP) .............................................. 9-240763
Oct. 14, 1997 (JP) .............................................. 9-280241

(51) Int. Cl.$^7$ ................................................. C07F 7/00
(52) U.S. Cl. .......................................... 556/55; 430/110
(58) Field of Search .............................. 556/55; 430/110

(56) References Cited

U.S. PATENT DOCUMENTS

| 3,884,949 A | | 5/1975 | Eicke et al. ................... 556/55 |
| 3,887,598 A | * | 6/1975 | Eicke et al. ................... 556/55 |
| 5,223,368 A | | 6/1993 | Ciccarelli et al. ........... 430/110 |
| 5,300,387 A | | 4/1994 | Ong ............................ 430/110 |

FOREIGN PATENT DOCUMENTS

| JP | 60-213959 | 10/1985 |
| JP | 62-99385 | 5/1987 |
| JP | 9-124659 | 5/1997 |

OTHER PUBLICATIONS

R.C. Paul, et al., Z. Anorg. Allg. Chem., vol. 423, pp. 91–97, "On Some Oxozirconium (IV) Compounds", 1976.

\* cited by examiner

*Primary Examiner*—Porfirio Nazario-Gonzalez
(74) *Attorney, Agent, or Firm*—Oblon, Spivak, McClelland, Maier & Neustadt, P.C.

(57) ABSTRACT

The present invention relates to a novel zirconium compound which is useful as a charge control agent for an electrophotographic toner. Further, it relates to an electrophotographic toner which contains said zirconium compound as a charge control agent.

3 Claims, 7 Drawing Sheets

ZIRCONIUM COMPOUND AND ELECTROPHOTOGRAPHIC TONER EMPLOYING IT

This application is a Division of application Ser. No. 09/297,568 Filed on May 4, 1999, now U.S. Pat. No. 6,410,198 B1.

TECHNICAL FIELD

The present invention relates to a novel zirconium compound. Further, it relates to a novel zirconium compound useful as a charge control agent for an electrophotographic toner which is used to develop an electrostatic latent image in the fields of electrophotography, electrostatic recording, etc., and an electrophotographic toner containing this compound.

BACKGROUND ART

In an image-forming process by means of an electrophotographic system, an electrostatic latent image is formed on a photoconductive material made of an inorganic or organic material, and the latent image is developed by a toner, then transferred and fixed on a paper sheet or plastic film to obtain a visible image. The photoconductive material may be positively electrifiable or negatively electrifiable depending upon its construction. When a printed portion is remained as an electrostatic latent image by exposure, development is conducted by means of an oppositely electrifiable toner. On the other hand, when a printed portion is destatisized for reversal development, development is conducted by means of an equally electrifiable toner.

A toner is composed of a binder resin, a coloring agent and other additives. However, in order to impart desired tribocharge properties (such as desired charge up speed, tribocharge level and tribocharge level stability), stability with time and environmental stability, it is common to use a charge-control agent. The properties of the toner will be substantially affected by this charge-control agent. When a positively electrifiable photoconductive material is used for development by an oppositely electrifiable toner, or when a negatively electrifiable photoconductive material is used for reversal development, a negatively electrifiable toner is used. In such a case, a negatively electrifiable charge-control agent is added.

Further, in a case of a color toner for which the market is expected to expand in future, it is necessary and indispensable to use a pale-colored or preferably colorless charge-control agent which does not affect the color of the toner. Such pale-colored or colorless charge-control agents may, for example, be metal complex salt compounds of salicylic acid derivatives (e.g. JP-B-55-42752, JP-A-61-69073, JP-A-61-221756 and JP-A-9-124659), aromatic dicarboxylic acid metal salt compounds (e.g. JP-A-57-111541), metal complex salt compounds of anthranilic acid derivatives (e.g. JP-A-62-94856) and organic boron compounds (e.g. U.S. Pat. No. 4,767,688 and JP-A-1-306861).

However, these charge-control agents have various drawbacks such that some of them are chromium compounds which are feared to be detrimental to environmental safety which is expected to be viewed as increasingly important, some of them are compounds which can not be made adequately colorless or pale-colored as required for toners, some of them have inadequate electrifying effects or provide oppositely electrifiable toners, or some of them are poor in dispersibility or chemical stability as compounds themselves. Thus, none of them has fully satisfactory properties as a charge-control agent.

Accordingly, it is an object of the present invention to provide a compound which is colorless or pale-colored and excellent in environmental safety and has a high safety as a compound and which is useful as a charge-control agent for an electrophotographic toner, and further to provide an electrophotographic toner which contains a compound excellent in the dispersibility in a binder resin, as a charge-control agent and which is excellent in the tribocharge property and capable of constantly presenting an image of high image quality.

DISCLOSURE OF THE INVENTION

In order to solve these problems, the present inventors have paid an attention to zirconium (Zr) being a tetravelent metal and have synthesized studied various compounds of a tetravalent cation or a bivalent cation being an oxo complex with salicylic acid or a salicylic acid derivative. They have found that compounds obtainable by such combinations are colorless stable compounds which specifically have good dispersibility in a binder resin and which are able to impart a good tribocharge property to an electrophotographic toner and that by using such compounds as charge control agents, it is possible to obtain an excellent electrophotographic toner which is capable of supplementing the drawbacks of conventional charge-control agents. The present invention has been accomplished on the basis of these discoveries.

Namely, the present invention provides a zirconium compound which is obtained from an aromatic hydroxycarboxylic acid or its salt and a compound containing zirconium, further an electrophotographic toner which contains such a zirconium compound as a charge-control agent, and further specifically a zirconium compound which is represented by the following Formula (1):

wherein $R_1$ is quaternary carbon, methine or methylene, and may contain a hetero atom of N, S, O or P, Y represents a cyclic structure linked by saturated bond(s) or unsaturated bond(s), each of $R_2$ and $R_3$ which are independent of each other, is an alkyl group, an alkenyl group, an alkoxy group, an aryl, aryloxy, aralkyl or aralkyloxy group which may have a substituent, a halogen group, hydrogen, a hydroxyl group, an amino group which may have a substituent, a carboxyl group, a carbonyl group, a nitro group, a nitroso group, a sulfonyl group or a cyano group, $R_4$ is hydrogen or an alkyl group, l is 0 or an integer of from 3 to 12, m is an integer of from 1 to 20, n is 0 or an integer of from 1 to 20, o is 0 or an integer of from 1 to 4, p is 0 or an integer of from 1 to 4, q is 0 or an integer of from 1 to 3, r is an integer of from 1 to 20, and s is an integer of from 1 to 20. And, the carbon number for the alkyl group, the alkenyl group and the alkoxy group is from 1 to 9.

Further, the present invention provides an electrophotographic toner containing the zirconium compound represented by the above Formula (1) as a charge-control agent, and an electrophotographic toner which contains a charge-control agent being a zirconium compound represented by the above Formula (1) within a range of from 0.01 to 10 parts by weight per 100 parts by weight of a resin. Further, a representative of the zirconium compound represented by the above Formula (1) is a zirconium compound of 3,5-di-t-butylsalicylic acid being a salicylic acid derivative, and the present invention provides an electrophotographic toner using such a compound as a charge control agents and further an electrophotographic toner wherein the average particle size of such a charge-control agent is within a range of from 0.01 μm to 10.0 μm.

Now, the present invention will be described in detail.

Figure 3:
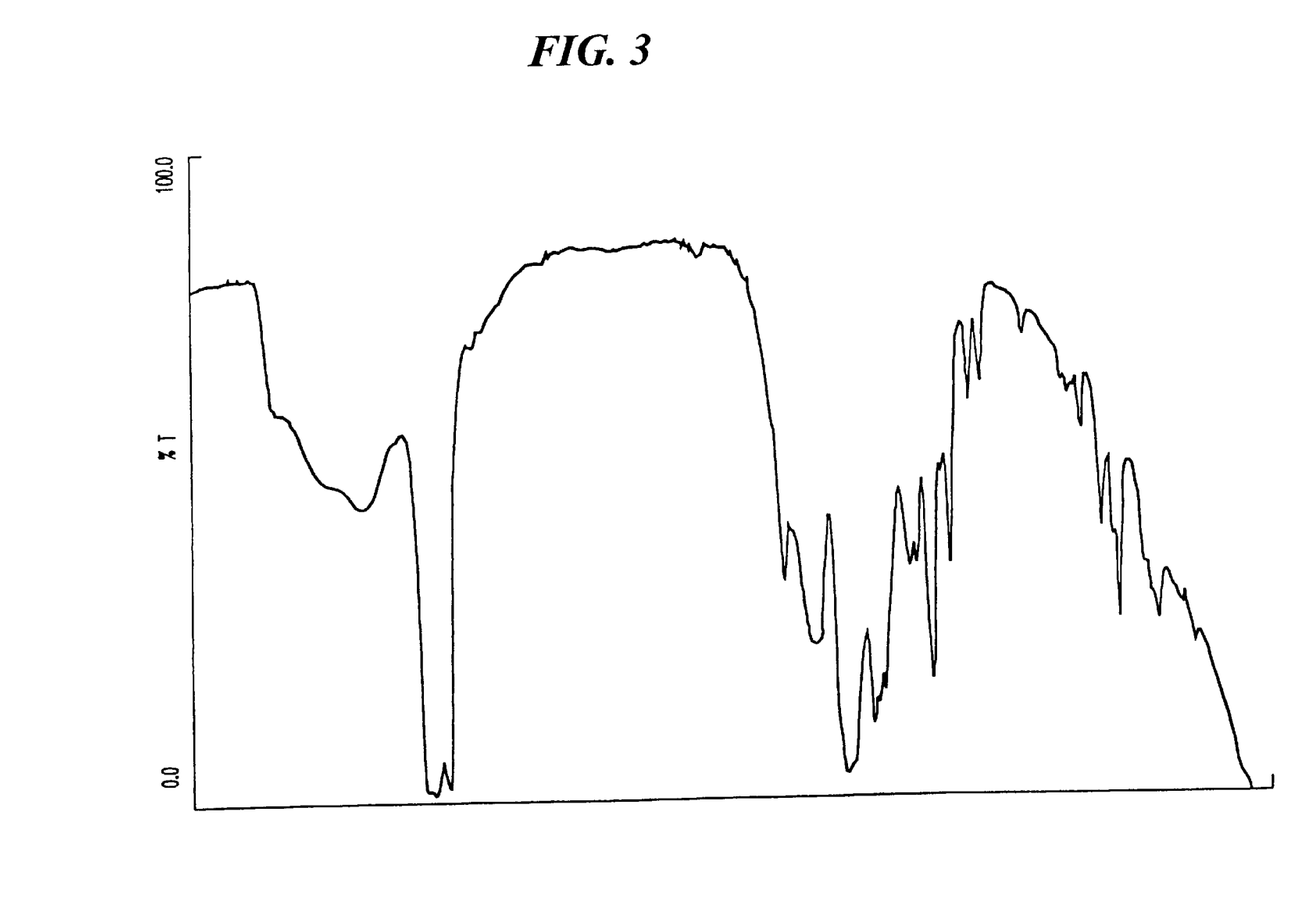
FIG. 3 is an IR chart (Nujol method, room temperature) of compound No. 1 of the present invention.
Figure 4:
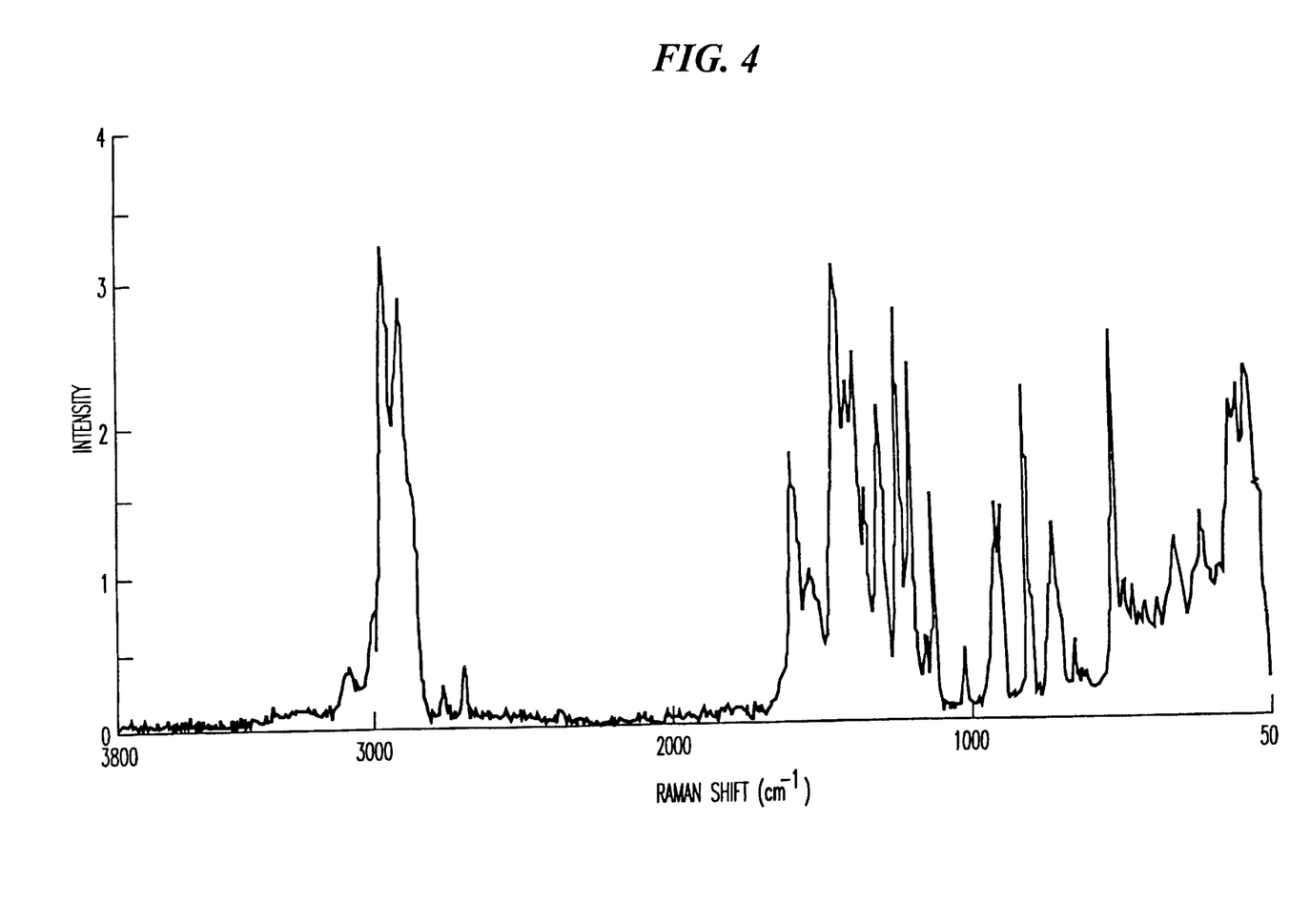
FIG. 4 is a Raman spectrum of compound No. 1 of the present invention.
Figure 5:
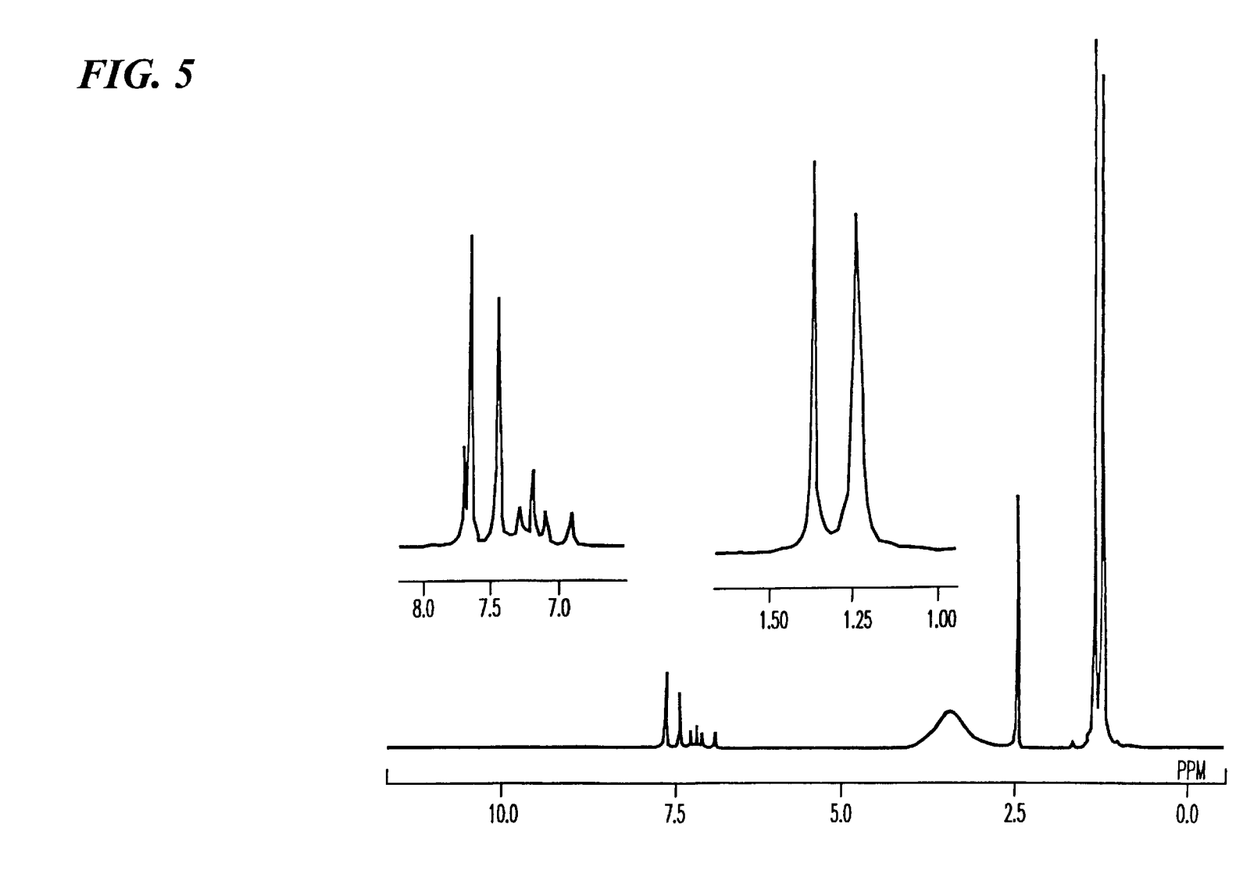
FIG. 5 is a proton NMR chart (solvent DMSO, measurement temperature 26.0° C.) of compound No. 2 of the present invention.
Figure 6:
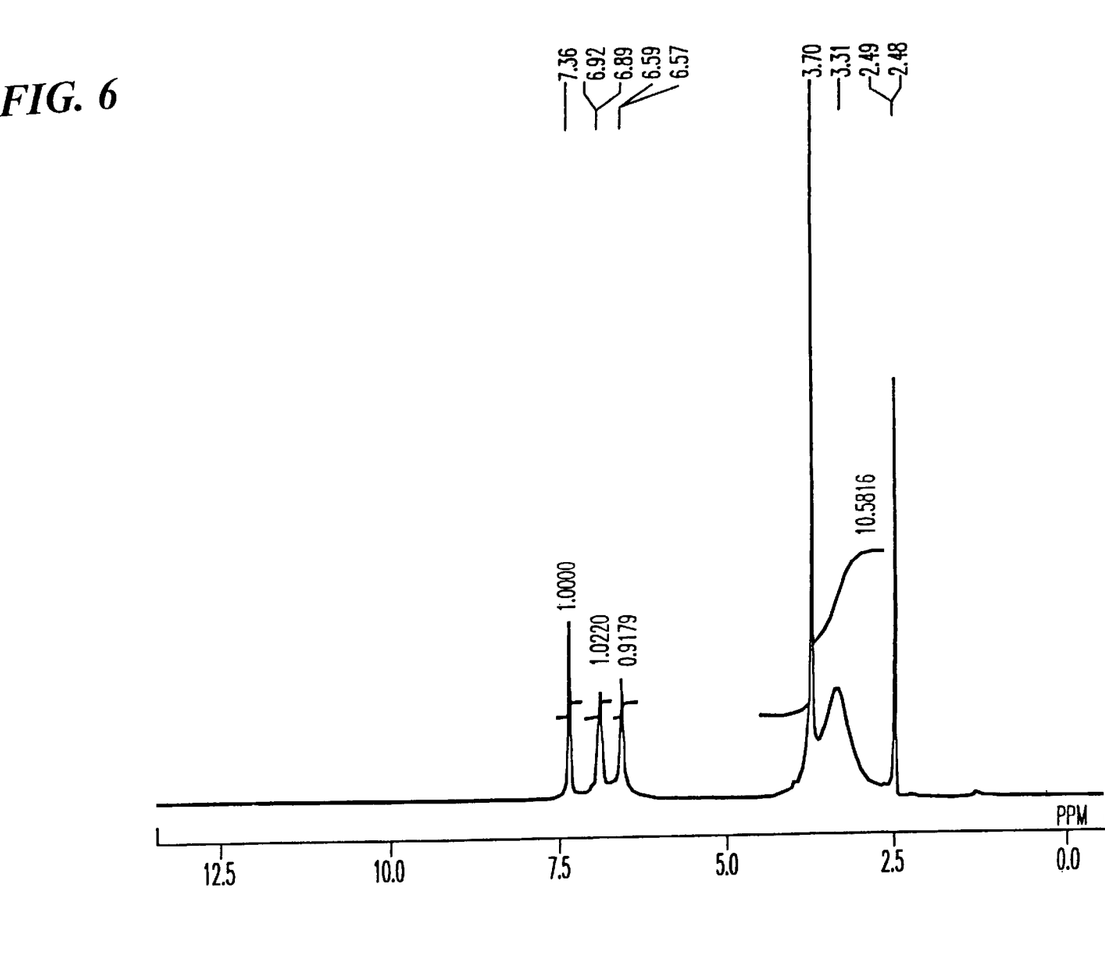
FIG. 6 is a proton NMR chart (solvent DMSO, measurement temperature 25.0° C.) of a proton NMR chart of compound No. 3 of the present invention. Further.
Figure 7:
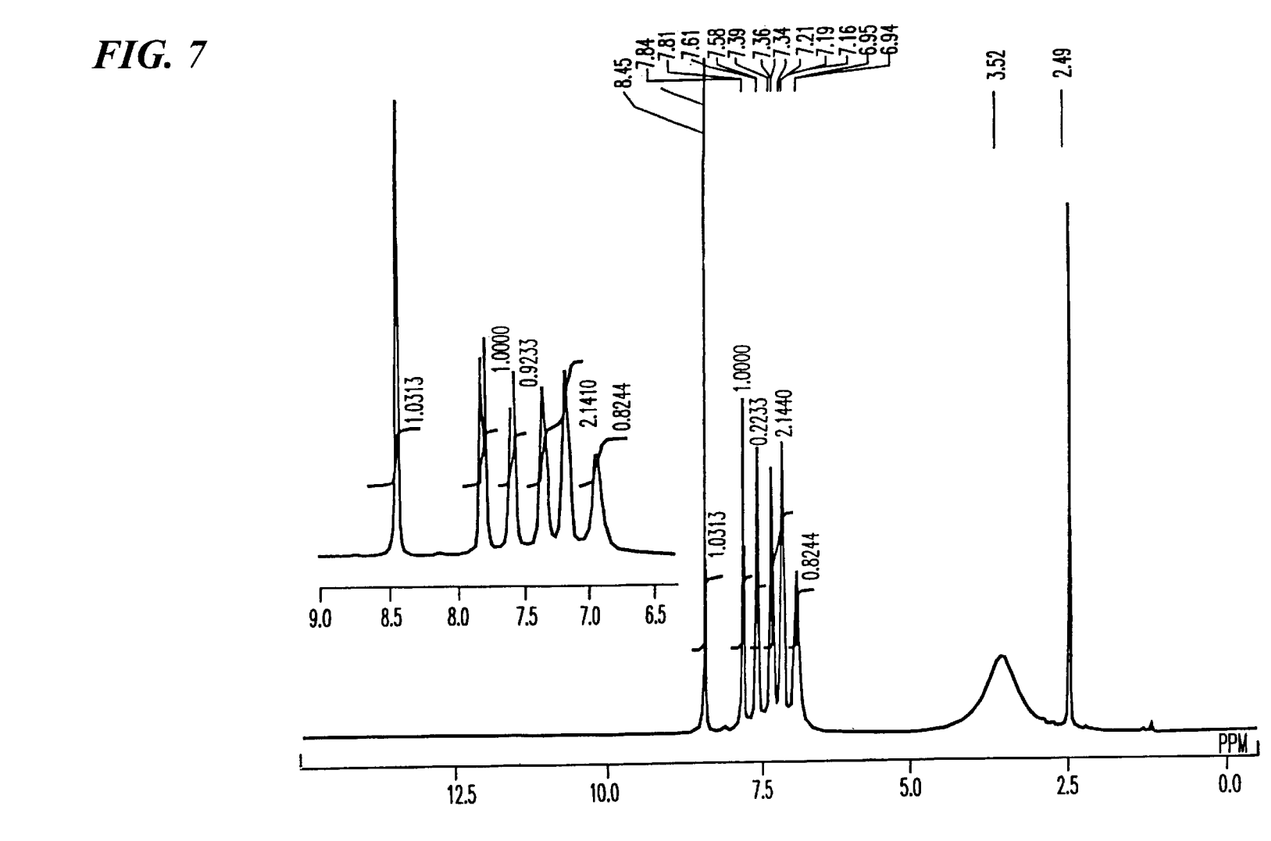
FIG. 7 is a proton NMR chart (solvent DMSO, measurement temperature 26.1° C.) of compound No. 4 of the present invention.

The zirconium compound of the present invention represented by the Formula (1) is a novel compound. The alkyl group, the alkenyl group and the alkoxy group in the Formula (1) is an alkyl group, an alkenyl group and an alkoxy group having a carbon number of from about 1 to about 9. The general formula of the zirconium compound of the present invention is supported by proton NMR charts of FIGS. 2, 5, 6 and 7, IR chart (Nujol method) of FIG. 3 and Raman Spectrum of FIG. 4.

The electrophotographic toner of the present invention basically comprises a binder resin, a coloring agent (pigment, dye or magnetic material) and a charge control agent comprising a compound of the Formula (1). Examples of a method for preparing the above electrophotographic toner include a method which comprises placing the above mixture in a heat-mixing apparatus to melt a binder resin, kneading, cooling, roughly pulverizing, finely pulverizing and classifying, a method which comprises dissolving the above mixture in a solvent, atomizing to prepare fine particles, drying and classifying, and a method which comprises polymerizing by dispersing a coloring agent and a compound of the Formula (1) in suspended monomer particles.

Examples of a binder resin include polystyrene, styrene-acryl type copolymer, styrene-methacrylate copolymer, styrene-propylene copolymer, styrene-butadiene copolymer, acrylic resin, styrene-maleic acid copolymer, olefin resin, polyester resin, epoxy resin, polyurethane resin, polyvinyl-butyral resin and the like, which are used respectively alone or in a mixture.

Examples of a coloring agent for a black toner include carbon black for a two-component type developer and a magnetic material for one-component type developer, and examples of a coloring agent for a color toner include those illustrated below.

Examples of a yellow coloring agent include an azo type organic pigment such as C.I. pigment yellow 1, C.I. pigment yellow 5, C.I. pigment yellow 12 and C.I. pigment yellow 17, an inorganic pigment such as yellow ocher, or an oil-soluble dye such as C.I. solvent yellow 2, C.I. solvent yellow 6, C.I. solvent yellow 14 and C.I. solvent yellow 19; examples of a magenta coloring agent include an azo pigment such as C.I. pigment red 57 and C.I. pigment red 57:1, a xanthene pigment such as C.I. pigment violet 1 and C.I. pigment violet 81, a thioindigo pigment such as C.I. pigment red 87, C.I. bat red 1 and C.I. pigment violet 38, or an oil-soluble dye such as C.I. solvent red 19, C.I. solvent red 49 and C.I. solvent red 52; and examples of a cyan coloring agent include a triphenylmethane pigment such as C.I. pigment blue 1, a phthalocyanine pigment such as C.I. pigment blue 15 and C.I. pigment blue 17, or an oil-soluble dye such as C.I. solvent blue 25, C.I. solvent blue 40 and C.I. solvent blue 70, and the like.

The compound of the present invention can be generally prepared by reacting with a metal-imparting agent in the presence of water and/or an organic solvent, filtrating a reaction product and then washing the product. Examples of the metal-imparting agent usable in the preparation of the compound of the present invention include, in a tetravalent cation form, a zirconium halide compound such as $ZrCl_4$, $ZrF_4$, $ZrBr_4$ and $ZrI_4$, $Zr(OR)_4$ (wherein R is an alkyl group, an alkenyl group or the like), or an inorganic zirconium compound such as $Zr(SO_4)_2$, and the like.

Examples of an oxo compound in a divalent cation form, include an inorganic acid zirconium compound such as $ZrOCl_2$, $ZrO(NO_3)_2$, $ZrO(ClO_4)_2$, $H_2ZrO(SO_4)_2$, $ZrO(SO_4)$ $Na_2SO_4$, and $ZrO(HPO_4)_2$, an organic acid zirconium compound such as $ZrO(CO_3)$, $(NH_4)_2ZrO(CO_3)_2$, $(NH_4)_2ZrO(C_2H_3O_2)_2$, $ZrO(C_2H_{35}O_2)_2$ and $ZrO(C_{18}H_{35}O_2)_2$, and the like.

The electrophotographic toner of the present invention may optionally contain other additives for protecting a photosensitive material and a carrier, improving cleaning properties, improving toner-flowing properties, adjusting thermal properties, electric properties and physical properties, adjusting resistance, adjusting a softening point and improving fixing properties, such as hydrophobic silica, a metal soap, fluorine type surfactant, dioctyl phthalate, a wax, an electroconductivity-imparting agent including tin oxide, zinc oxide, carbon black or antimony oxide, and an inorganic fine powder such as titanium oxide, aluminum oxide or alumna.

Examples of carbon black usable in the present invention include channel black, furnace black and the like, and the carbon black is usable regardless of pH, particle size and hue. Further, the carbon black is not limited to carbon black used for conventional toners, but usable if it satisfies blackness as a toner.

Also, in order to impart hydrophobic properties or to control an electrified amount, the inorganic fine powder used in the present invention may optionally be treated with a treating agent such as a silicone varnish, various modified silicone vanishes, a silicone oil, various modified silicone oils, a silane coupling agent, a silane coupling agent having a functional group and other organic silicon compounds, or a mixture of these treating agents. Also, the toner of the present invention may further contain a small amount of a lubricant such as Teflon, zinc stearate and polyvinylidene fluoride, an abrasive material such as cesium oxide, silicon carbide and strontium titanate, an anti-caking agent, or white or black fine particles having a polarity opposed to that of the toner particles for improving developing properties.

In the case of using the toner of the present invention for a two-component type developer, examples of a carrier to be used include a binder type carrier having fine glass beads, iron powder, ferrite powder, nickel powder or magnetic particles dispersed in resin particles, or a resin-coated carrier having the surface of the above fine particles coated with polyester type resin, fluorine type resin, vinyl type resin, acryl type resin or silicone type resin. The compound of the Formula (1) of the present invention and the toner containing this compound provides excellent properties when used as a one-component type toner. Further, they can be used for a capsule toner and a polymerized toner.

Examples of the magnetic material usable in the toner of the present invention include metal fine powder of iron, nickel or cobalt, an alloy of iron, lead, magnesium, antimony, beryllium, bismuth, cadmium, calcium, manganese, selenium, titanium, tungsten, vanadium, cobalt, copper, aluminum, nickel or zinc, a metal oxide such as aluminum oxide, iron oxide or titanium oxide, a ferrite of iron, manganese, nickel, cobalt or zinc a nitride such as vanadium nitride or chromium nitride, a carbide such as tungsten carbide or silicon carbide, and a mixture of these materials. Preferable examples of the magnetic material include iron oxide such as magnetite, hematite or ferrite, but the charge control agent used in the present invention provides a satisfactory electrochargeability regardless of the magnetic material used.

Further, the charge control agent used in the present invention may be used in combination with conventionally known materials such as compounds obtained from 3,5-di-t-butylsalicylic acid and chromium, zinc or aluminum (tradename: Bontron E-81, E-84 and E-88 manufactured by Orient Kagaku Kogyo K.K.).

Still further, the compound of the Formula (1) of the present invention can be satisfactorily used as an electric charge-imparting agent for an electrostatic powder coating paint. Thus, the electrostatic powder coating paint using this electric charge-imparting agent is excellent in environmental resistance and storage stability, particularly excellent in thermal stability and durability, and achieves a coating efficiency of 100% and forms a thick film having no coating defects.

BEST MODE FOR CARRYING OUT THE INVENTION

Now, the present invention is concretely described with reference to Preparation Examples of a compound and Examples of a toner. In the following Preparation Examples and Examples, "part" means "part by weight".

PREPARATION EXAMPLE 1

Reaction between 3,5-di-t-butylsalicylic acid and zirconium oxide compound (synthesis of compound No. 1)

33 parts of 3,5-di-t-butylsalicylic acid and 19 parts of 25% caustic soda were dissolved in 350 parts of water, and the mixture was heated to 50° C. with stirring, and a solution having 19 parts of zirconium oxychloride ($ZrOCl_2 \cdot 8H_2O$) dissolved in 90 parts of water was dropwise added thereto (precipitation of white crystal). The resultant mixture was stirred at the same temperature for 1 hour, and was cooled to room temperature, and about 6 parts of 25% caustic soda was added thereto to adjust a pH in the range of 7.5 to 8.0. Crystal thus precipitated was filtrated out, washed with water and dried to obtain 25 parts of white crystal. This compound had a melting point of at least 300° C. The compound thus obtained was subjected to proton NMR measurement to obtain a spectrum illustrating the properties of the aimed product. The results of elemental analysis were as follows:

|  | Carbon (%) | Hydrogen (%) | Nitrogen (%) | Zirconium (%) |
| --- | --- | --- | --- | --- |
| Theoretical value | 49.1 | 6.6 | 0.0 | 19.9 |
| Measured value | 50.0 | 6.2 | 0.0 | 19.8 |

Further, according to IR measurement, an absorbing band resulted from Zr—OH and a hydroxyl group of salicylic acid derivative was observed at 3,200–3,600 $cm^{-1}$ and a carbonyl absorbing band showing a bond between zirconium and salicylic acid derivative was observed in the vicinity of 1,530 $cm^{-1}$. According to Raman Spectrum measurement, an absorbing band resulted from a bond formed between zirconium and 3,5-di-t-butylsalicylic acid was observed at 700–800 $cm^{-1}$. According to these analytical results, compound No. 1 is considered to have the following structure ($L_1$=3,5-di-t-butylsalicylic acid).

PREPARATION EXAMPLE 2

Reaction between 3,5-di-t-butylsalicylic acid and zirconium (IV) isopropoxide (synthesis of compound No. 2)

100 parts of 3,5-di-t-butylsalicylic acid and 39.0 parts of zirconium (IV) isopropoxide were dissolved in 100 parts of toluene, and were refluxed for 6 hours. The reaction mixture was cooled to room temperature, and toluene was concentrated under vacuum, and 5 parts of methanol was added to the resultant residue to precipitate crystal. The crystal thus precipitated was filtrated out, and washed with methanol and was dried to obtain 55.0 parts of white crystal. This compound had a melting point of at least 295° C. Further, this compound was subjected to proton NMR measurement to obtain a spectrum illustrating the properties of the aimed product. The results of elemental analysis of this compound were as follows:

|  | Carbon (%) | Hydrogen (%) | Nitrogen (%) | Zirconium (%) |
| --- | --- | --- | --- | --- |
| Theoretical value | 66.2 | 7.8 | 0.0 | 8.4 |
|  | 66.4 | 7.7 | 0.0 | 8.1 |

According to these analytical results, compound No. 2 was considered to have the following structure ($L_1$=3, 5-di-t-butylsalicylic acid).

PREPARATION EXAMPLE 3

Reaction between 5-methoxysalicylic acid and zirconium oxide compound (synthesis of compound No. 3)

19 parts of 5-methoxysalicylic acid and 19 parts of 25% caustic soda were dissolved in 350 parts of water, and the resultant mixture was heated to 50° C. with stirring, and a solution having 19 parts of zirconium oxychloride ($ZrOCl_2 \cdot 8H_2O$) dissolved in 90 parts of water was dropwise added thereto (precipitation of light brown white crystal). The resultant mixture was stirred at the same temperature for 1 hour, and was cooled to room temperature, and about 6 parts of 25% caustic soda was added thereto to adjust a pH value in the range of from 7.5 to 8.0. Crystal thus precipitated was filtrated out, and was washed with water and dried to obtain 15 parts of light brown write crystal. This compound had a melting point of at least 300° C. Also, the compound was subjected to proton NMR measurement to obtain a spectrum showing properties of the aimed product. The results of elemental analysis were as follows:

|  | Carbon (%) | Hydrogen (%) | Nitrogen (%) | Zr (%) |
|---|---|---|---|---|
| Theoretical value | 36.3 | 3.3 | 0.0 | 27.8 |
| Measured value | 36.9 | 3.1 | 0.0 | 27.4 |

According to these analytical results, compound No. 3 is considered to have the following structure ($L_2$=5-methoxysalicylic acid).

PREPARATION EXAMPLE 4

Reaction between 2-hydroxy-3-naphthoic acid and zirconium oxide compound (synthesis of compound No. 4)

21 parts of 2-hydroxy-3-naphthoic acid and 19 parts of 25% caustic soda were dissolved in 350 parts of water, and the resultant mixture was heated to 50° C. with stirring, and a solution having 19 parts of zirconium oxychloride ($ZrOCl_2 \cdot 8H_2O$) dissolved in 90 parts of water was dropwise added thereto (precipitation of light yellow crystal). Then, the resultant mixture was stirred at the same temperature for 1 hour, and cooled to room temperature, and about 6 parts of 25% caustic soda was added to the mixture to adjust a pH value in the range of 7.5 to 8.0. Crystal thus precipitated was filtrated out, and was washed with water and dried to obtain 16 parts of light yellow crystal. This compound had a softening point of at least 300° C. Also, this compound was subjected to proton NMR measurement to obtain a spectrum showing the properties of the aimed product. The results of elemental analysis were as follows:

|  | Carbon (%) | Hydrogen (%) | Nitrogen (%) | Zr (%) |
|---|---|---|---|---|
| Theoretical value | 43.1 | 3.6 | 0.0 | 24.0 |
| Measured value | 43.8 | 3.5 | 0.0 | 23.6 |

According to these analytical results, compound No. 4 is considered to have the following structure ($L_3$=2-hydroxy-3-naphthoic acid).

Examples of other zirconium compounds synthesized in the same manner as in the above Preparation Examples 1 to 4 are illustrated in the following Table 1, but the present invention is not limited thereto.

TABLE 1

| Compound No. | Salicylic acid derivatives as a ligand (referred to as "L") | Metal-imparting agent | L:Zr |
|---|---|---|---|
| 5 | i-Pro, COOH, OH, i-Pro (benzene ring) | $ZrOCl_2$ | 5:4 |
| 6 | t-Bu, COOH, OMe, t-Bu (benzene ring) | $ZrOCl_2$ | 5:4 |
| 7 | t-Bu, COOH, OH (naphthalene ring) | $ZrOCl_2$ | 5:4 |
| 8 | $H_3C$, COOH, OMe, t-Bu (benzene ring) | $ZrOCl_2$ | 5:4 |
| 9 | Cl, COOH, OH, Cl (benzene ring) | $ZrOCl_2$ | 5:4 |

TABLE 1-continued

| Compound No. | Salicylic acid derivatives as a ligand (referred to as "L") | Metal-imparting agent | L:Zr |
|---|---|---|---|
| 10 | 2-hydroxybenzoic acid (salicylic acid) with COOH and OH on benzene | ZrOCl$_2$ | 5:4 |
| 11 | 3,5-di-i-Pr salicylic acid | ZrCl$_4$ | 4:1 |
| 12 | 3-t-Bu-5-OMe salicylic acid with t-Bu | ZrCl$_4$ | 4:1 |
| 13 | 3-hydroxy-2-naphthoic acid | ZrCl$_4$ | 4:1 |
| 14 | 3-CH$_3$-5-t-Bu-OMe salicylic acid | Zr(i-PrO)$_4$ | 4:1 |
| 15 | 3,5-dichloro salicylic acid | Zr(i-PrO)$_4$ | 4:1 |
| 16 | 5-OCH$_3$ salicylic acid (H$_3$CO-) | Zr(i-PrO)$_4$ | 4:1 |
| 17 | salicylic acid | Zr(i-PrO)$_4$ | 4:1 |

Note: Zr(i-PrO)$_4$ = Zirconium (IV) isopropoxide

EXAMPLE 1

1 part of compound No. 1, 5 parts of carbon black (MA-100 manufactured by Mitsubishi Chemical Corporation) and 94 parts of styrene-acryl copolymer resin (CPR-100 manufactured by Mitsui Chemicals, Inc.) were kneaded in a heat-mixing apparatus, and the kneaded product was cooled and was roughly pulverized by a hammer mill. The resultant product was further finely pulverized by a jet mill and was classified to obtain a black toner having a particle size of from 10 to 12 μm. 4 parts of the toner thus obtained was mixed with 100 parts of silicon-coat type ferrite carrier (F-96-100 manufactured by Powder Tech K.K.) and the resultant mixture was agitated to obtain a toner negatively charged at a charged amount of −17.5 μC/g measured by a blow-off powder charged amount-measuring apparatus. The toner thus obtained was applied to a modified commercially available copying machine to obtain an image, and a clear image could be obtained from the first copy and also after copying 10,000 times.

EXAMPLE 2

1 part of compound No. 1, 5 parts of carbon black (KA-100 manufactured by Mitsubishi Chemical Corporation) and 94 parts of polyester resin (HP-301 manufactured by Nihon Gosei Kagaku K.K.) were kneaded in a heat mixing apparatus, and the kneaded product was cooled and was roughly pulverized by a hammer mill. The resultant product was further finely pulverized by a jet mill and was classified to obtain a black toner having a particle size of from 10 to 12 μm. 4 parts of the toner thus obtained was mixed with 100 parts of a silicon-coat type ferrite carrier (F-96-100 manufactured by Powder Tech K.K.) and the mixture was agitated to obtain a toner negatively charged at a charged amount of −18.0 μC/g measured by a blow-off powder charged amount-measuring apparatus. The toner thus obtained was applied to a modified commercially available copying machine to obtain an image, and a clear image could be obtained from the first copy and also after copying 10,000 times.

EXAMPLE 3

1 part of compound No. 2, 5 parts of carbon black (MA-100 manufactured by Mitsubishi Chemical Corporation) and 94 parts of styrene-acryl copolymer resin (CPR-100 manufactured by Mitsui Chemicals, Inc.) were kneaded in a heat-mixing apparatus, and the kneaded product was cooled and was roughly pulverized by a hammer mill. The resultant product was further finely pulverized by a jet mill and was classified to obtain a black toner having a particle size of from 10 to 12 μm. 4 parts of the toner thus obtained was mixed with 100 parts of a silicon-coat type ferrite carrier (F-96-100 manufactured by Powder Tech K.K.) and the mixture was agitated to obtain a toner negatively charged at a charged amount of −15.2 μC/g measured by a blow-off powder charged amount-measuring apparatus. The toner thus obtained was applied to a modified commercially available copying machine to obtain an image, and a clear image could be obtained from the first copy and also after copying 10,000 times.

EXAMPLE 4

1 part of compound No. 3, 5 parts of carbon black (MA-100 manufactured by Mitsubishi Chemical Corporation) and 94 parts of polyester resin (HP-301 manufactured by Nihon Gosei Kagaku K.K.) were kneaded in a heat-mixing apparatus, and the kneaded product was cooled and was roughly pulverized by a hammer mill. The resulting product was further finely pulverized by a jet mill and was classified to obtain a black toner having a particle size of from 10 to 12 μm. 4 parts of the toner thus obtained was mixed with 100 parts of a silicon-coat type ferrite carrier (F-96-100 manufactured by Powder Tech K.K.) and the resultant mixture was agitated to obtain a toner negatively charged at a charged amount of −17.0 μC/g measured by a blow-off powder charged amount-measuring apparatus. The toner thus obtained was applied to a modified commercially available copying machine to obtain an image, and a clear image could be obtained from the first copy and also after copying 10,000 times.

EXAMPLE 5

1 part of compound No. 4, 5 parts of carbon black (MA-100 manufactured by Mitsubishi Chemical Corporation) and 94 parts of styrene-acryl copolymer resin (CPR-100 manufactured by Mitsui Chemicals, Inc.) were kneaded in a heat-mixing apparatus, and the kneaded product was roughly pulverized by a hammer mill. The resultant product was further finely pulverized by a jet mill and was classified to obtain a black toner having a particle size of from 10 to 12 $\mu$m. 4 parts of the toner thus obtained was mixed with 100 parts of a silicon-coat type ferrite carrier (F-96-100 manufactured by Powder Tech K.K.), and the resultant mixture was agitated to obtain a toner negatively charged at a charged amount of $-17.2$ $\mu$C/g measured by a blow-off powder charged amount-measuring apparatus. The toner thus obtained was applied to a modified commercially available copying machine to obtain an image, and a clear image could be obtained from the first copy and also after copying 10,000 times.

EXAMPLE 6

1 part of compound No. 1, 50 parts of magnetic powder (BL-200 manufactured by Toda Kogyo K.K.) and 50 parts of styrene-acryl copolymer resin (CPR-100 manufactured by Mitsui Chemicals, Inc.) were kneaded in a heat-mixing apparatus, and the kneaded product was cooled and was roughly pulverized by a hammer mill. The resultant product was further finely pulverized by a jet mill and was classified to obtain a black toner having a particle size of from 10 to 12 $\mu$m. 4 parts of the toner thus obtained was mixed with 100 parts of a non-coated ferrite carrier (F-100 manufactured by Powder Tech K.K.), and the resultant mixture was agitated to obtain a toner negatively charged at a charged amount of $-16.8$ $\mu$C/g measured by a blow-off powder charged amount-measuring apparatus. The toner thus obtained was applied to a commercially available copying machine to obtain an image, and a clear image could be obtained from the first copy and also after copying 10,000 times.

COMPARATIVE EXAMPLE

Reaction between 3,5-di-t-butylsalicylic acid and zinc chloride (synthesis of comparative compound No. 1)

4 parts of 3,5-di-t-butylsalicylic acid was dispersed in 50 parts of water, and a solution having 1.5 parts of sodium hydroxide dissolved in 20 parts of water was added thereto. The resultant mixture was stirred at 60° C. for 0.5 hour, and a solution having 1.1 parts of zinc chloride dissolved in 20 parts of water was dropwise added thereto, and the resultant mixture was stirred at 45° C. for 1 hour. The resultant mixture was cooled to room temperature, and a 2N hydrochloric acid aqueous solution was added thereto to adjust the resultant solution at a pH of 6, and a precipitated product was filtrated out and was washed with water to obtain 4 parts of a comparative compound. The comparative compound thus obtained had a softening point of at least 300° C. The comparative compound was subjected to proton NMR measurement to obtain a spectrum showing the properties of the aimed product. The results of elemental analysis were as follows:

|  | Carbon (%) | Hydrogen (%) | Nitrogen (%) | Zinc (%) |
|---|---|---|---|---|
| Theoretical value | 63.9 | 7.5 | 0.0 | 11.6 |
| Measured value | 64.2 | 7.6 | 0.0 | 11.4 |

1 part of comparative compound No. 1, 5 parts of carbon black (MA-100) and 94 parts of styrene-acryl copolymer resin (CPR-100) were kneaded in a heat-mixing apparatus, and the kneaded product was cooled and was roughly pulverized by a hammer mill. The resultant product was further finely pulverized by a jet mill and was classified to obtain a black toner having a particle size of from 10 to 12 $\mu$m. 4 parts of the toner thus obtained was mixed with 100 parts of silicon-coat type ferrite carrier (F-96-100), and the resultant mixture was agitated to obtain a toner negatively charged at a charged amount of $-8.5$ $\mu$C/g measured by a blow-off powder charged amount-measuring apparatus.

Figure 1:
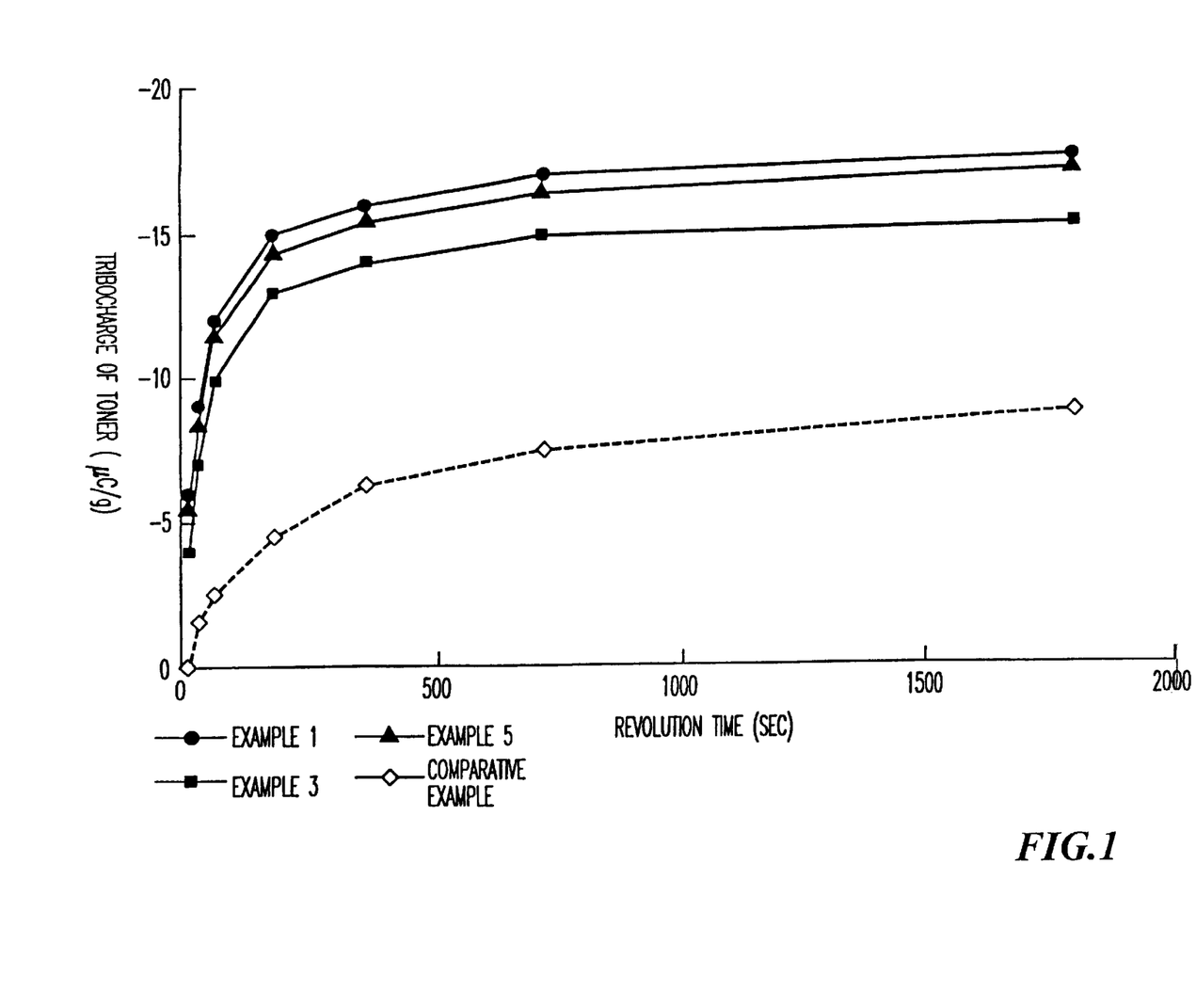
FIG. 1 illustrates a tribo charge amount of a toner using a zirconium compound of the present invention in comparison with that of a toner using a zinc compound.
Figure 2:
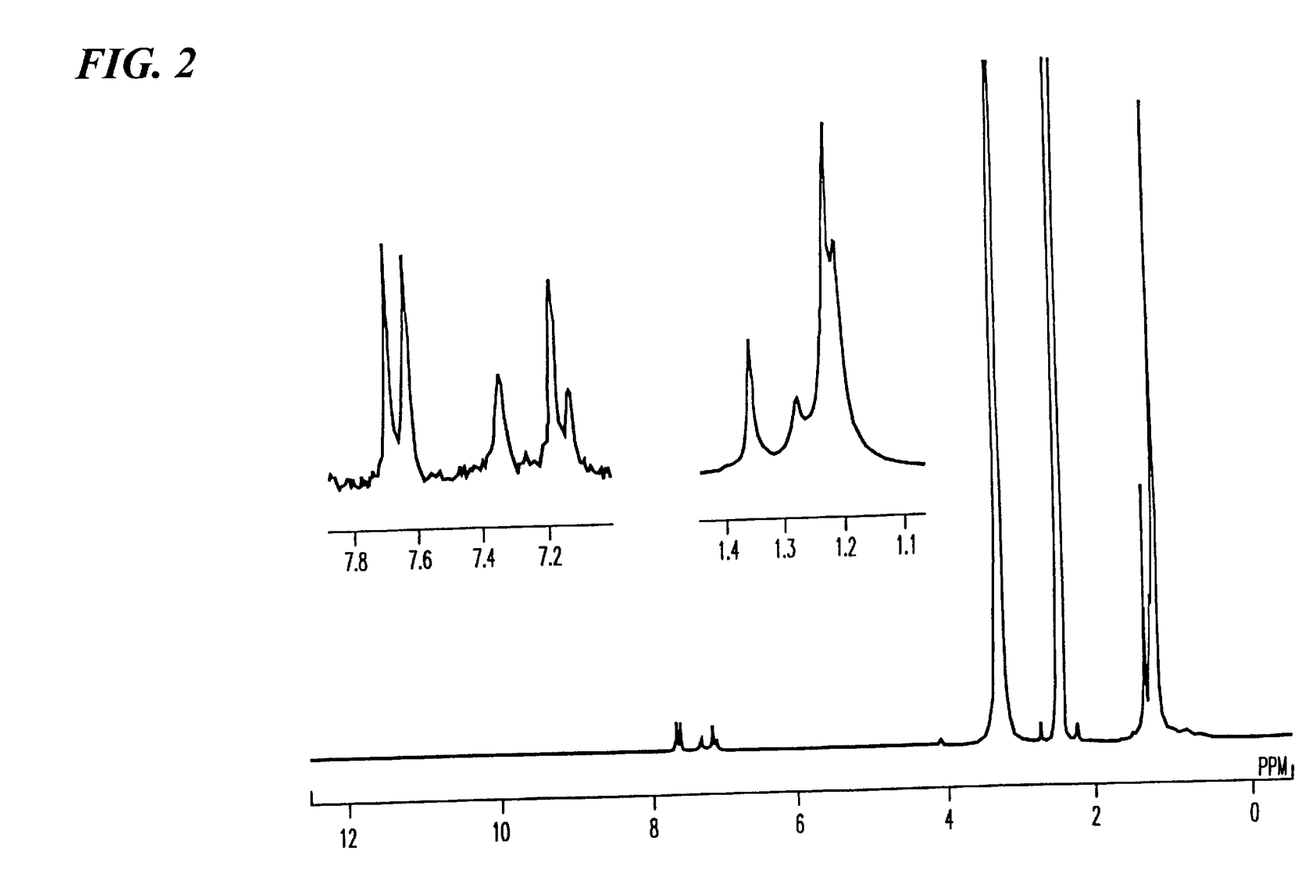
FIG. 2 is a proton NMR chart (solvent DMSO, measurement temperature 25.9° C.) of compound No. 1 of the present invention.

Copying test results of compounds No. 5 to No. 17 and Comparative Example 1 are shown in the following Table 2, and simulation results of charged amounts of compounds No. 1, No. 2 and No. 4 and comparative compound No. 1 are shown in FIG. 1.

TABLE 2

| Example | Compound No. | Charged amount *1 CPR-100 | Charged amount *1 HP-301 | Image quality First copy | Image quality 10,000th copy | Environmental stability |
|---|---|---|---|---|---|---|
| 7 | 5 | −16.0 | −17.2 | Clear | Clear | ◯ |
| 8 | 6 | −17.1 | −17.2 | Clear | Clear | ◯ |
| 9 | 7 | −14.2 | −16.9 | Clear | Clear | ◯ |
| 10 | 8 | −17.2 | −16.9 | Clear | Clear | ◯ |
| 11 | 9 | −15.6 | −17.6 | Clear | Clear | ◯ |
| 12 | 10 | −14.9 | −16.5 | Clear | Clear | ◯ |
| 13 | 11 | −15.9 | −16.3 | Clear | Clear | ◯ |
| 14 | 12 | −17.2 | −17.2 | Clear | Clear | ◯ |
| 15 | 13 | −14.5 | −16.3 | Clear | Clear | ◯ |
| 16 | 14 | −16.7 | −17.3 | Clear | Clear | ◯ |
| 17 | 15 | −15.2 | −16.9 | Clear | Clear | ◯ |
| 18 | 16 | −16.9 | −16.3 | Clear | Clear | ◯ |
| 19 | 17 | −15.8 | −16.2 | Clear | Clear | ◯ |
| Comparative Example | Comparative compound No. 1 | −8.5 | −8.7 | Clear | Partly fogged | Δ |

*1: 1 $\mu$C/g, 30 min., 1% addition; a carrier used was a silicon coat type carrier (F-96-100)

INDUSTRIAL APPLICABILITY

The zirconium compound of the present invention is a colorless or pale color compound having a high stability, and is particularly useful as a charge control agent for an electrophotographic toner since it has a satisfactory dispersibility to a binder resin of an electrophotographic toner and imparts a satisfactory chargeability to the toner. Also, an electrophotographic toner containing the compound of the present invention as a charge control agent constantly and stably provides an image of high quality.

What is claimed is:
1. A zirconium compound represented by the following formula (2):

(2)

wherein t-Bu is a tertiary butyl group, m is an integer of from 1 to 20, s is an integer of from 1 to 20 and r is an integer of from 3 to 20.

2. A zirconium compound which is represented by the following formula (3):

(3)

wherein $R_1$ and $R_2$ are hydrogen or an alkyl group, l is 0 or an integer of from 1 to 4, o is 0 or an integer of from 1 to 4, m is an integer of from 1 to 20, s is an integer of from 1 to 20, r is an integer of from 1 to 20, and r/m=5/4.

3. The zirconium compound according to claim 2, wherein the zirconium compound is represented by the following formula (4):

(4)

wherein t-Bu is a tertiary butyl group, m is an integer of from 1 to 20, s is an integer of from 1 to 20, r is an integer of from 1 to 20, and r/m=5/4.

* * * * *